United States Patent
Yarosh

[11] Patent Number: 6,103,746
[45] Date of Patent: Aug. 15, 2000

[54] METHODS AND COMPOSITIONS FOR THE PROTECTION OF MITOCHONDRIA

[75] Inventor: Daniel B. Yarosh, Freeport, N.Y.

[73] Assignee: Oxis International, Inc., Portland, Oreg.

[21] Appl. No.: 09/026,198

[22] Filed: Feb. 19, 1998

(Under 37 CFR 1.47)

Related U.S. Application Data

[60] Provisional application No. 60/038,749, Feb. 20, 1997.

[51] Int. Cl.$^7$ .................................................. A61K 31/415
[52] U.S. Cl. ........................................... 514/398; 424/9.1
[58] Field of Search .............................. 514/398; 424/9.1

[56] References Cited

U.S. PATENT DOCUMENTS

| | | | |
|---|---|---|---|
| 4,898,878 | 2/1990 | Shapiro et al. | 514/386 |
| 5,190,762 | 3/1993 | Yarosh | 424/450 |
| 5,272,166 | 12/1993 | Breslow et al. | 514/390 |
| 5,438,151 | 8/1995 | Yadan et al. | 548/324.1 |

FOREIGN PATENT DOCUMENTS

| | | |
|---|---|---|
| 61-155302 | 7/1986 | Japan . |
| 63-008335 | 1/1988 | Japan . |
| WO 94/04129 | 3/1994 | WIPO . |

OTHER PUBLICATIONS

Akamnu et al, 1991, Arch Biochem Biophys, 298:10–6.
Aruoma et al. (1997) Biochem. Biophys. Res. Comm. 231:389–91.
Asmus et al, 1996, Biochem J , 315:625–9.
Hartman, 1990, Methods in Enzymology, 186:310–8.
Hartman, 1988, Radiation Research, 114:319–30.
Hartman, Interception of toxic agents/mutagens/carcinogens, pp. 169–179.
Hartman (1987) Environ. Mol. Mutag. 10:3–15.
Langer, 1990, Science, 249:1527–33.
Lopez–Berestein, in Liposomes in the Therapy of Infectious Disease and Cancer, Liss: New York, pp. 317–327.
Treat et al, 1989, in Liposomes in the Therapy of Infectious Disease and Cancer, pp. 353–365.
Van den Broeke et al, 1993, J Photochem Photobiol B, 178:279–86.
Van den Broeke et al, 1993, Int J Radia Biol, 63:493–500.
Akanmu et al, Archiv. Biochemistry &Biophysics, vol. 288, #1, pp. 10–16, 1991.

*Primary Examiner*—James H. Reamer
*Attorney, Agent, or Firm*—Klauber & Jackson

[57] ABSTRACT

Protection of mitochondria from oxidative damage due to natural or disease processes as well as by the effects of exogenous factors such as incident sunlight, exposure via inhalation to oxidative environmental toxins, consumption of dietary oxidants, and oxidative-stress-inducing pharmaceuticals, exposure to radiation including radiation therapy, among others, is provided by a composition comprising L-ergothioneine. L-ergothioneine may be prepared in a pharmaceutically-acceptable carrier to form an agent for topical application to the skin, and for orally or parenteral administration. Effective application and delivery of L-ergothioneine is enhanced by encapsulation in a liposome, a preferred embodiment. Diagnostic methods for determining exposure and susceptibility to radiation, radical, and reactive oxygen species in mammals is also provided.

32 Claims, No Drawings

METHODS AND COMPOSITIONS FOR THE PROTECTION OF MITOCHONDRIA

CROSS-REFERENCE TO RELATED APPLICATION

This application claims benefit of Provisional Application No. 60/038,749, filed Feb. 20, 1997, which is incorporated herein by reference in its entirety.

BACKGROUND OF THE INVENTION

Mitochondria are subcellular organelles present in all oxygen-utilizing organisms in which energy in the form of adenosine triphosphate (ATP) is generated, and oxygen in reduced to water. Ninety percent of the oxygen taken in is consumed in mitochondria. A substantial byproduct of this ATP generation is the formation of potentially toxic oxygen radicals. For example, it is estimated that 1–2% of all reduced oxygen yields superoxide ($O_2$-) and hydrogen peroxide ($H_2O_2$). Other reactive oxygen species (ROS) that form are singlet oxygen ($^1O_2$) and hydroxyl radical (OH•). Under stress conditions in the cell this can rise to 10% of all consumed oxygen. Mitochondrial membranes are sensitive to lipid peroxidation and depolarization resulting from these ROS. Mitochondrial damage is also a result of exposure to sunlight, which forms ROS as indicated above. Because damage to mitochondria is believed to be the cause or an important factor in some diseases, such as cancer, diabetes, cataract, neurodegenerative disease, porphyrias, cardiovascular disease, and also a contributor to the complications of aging, a method of protecting mitochondria from such damage, repairing such damage, is desired. Cellular damage from burns to the skin and lungs from contact with or exposure to fire and other sources of intense heat is mediated through radical damage. Furthermore, exposure to adverse environmental factors, including industrial air pollutants and petroleum and tobacco combustion products, may contribute to oxidative damage to pulmonary and other tissues of the body. In addition, various therapeutic regimens such as chemotherapeutic drugs and radiation therapy for the treatment of dysproliferative diseases induce significant oxidant-stress-related side effects, such as cardiotoxicity. The present invention relates to applied agents which protect the mitochondria from such damage.

L-ergothioneine is a sulphur-containing amino acid which is found in many mammalian tissues but is not endogenously synthesized and must be consumed in the diet. Although it exists in some tissues in millimolar quantities, its exact role is uncertain (see: Melville, 1959, Vitamins and Hormones 7:155–204). It is generally regarded as an antioxidant, although results are conflicting. Some regard it as a scavenger of hydrogen peroxide (see: Hartman, 1990, Methods in Enzymology 186:310–318), while others contend that it does not readily react with hydrogen peroxide but does scavenge hydroxyl radical (see: Akamnu et al., 1991, Arch. Biochem. Biophys. 298:10–16, 1991). Although previous in vitro studies have demonstrated its ability to protect DNA and proteins against phototoxic drug binding induced by UV radiation (e.g., van den Broeke et al., 1993, J. Photochem. Photobiol. B 17:279–286), and to protect bacteriophage against gamma-irradiation ( Hartman et al., 1988, Radiation Research 114:319–330), in vivo results have not been as promising. Although L-ergothioneine has been claimed as useful in topical formulations for scavenging radicals and UV light protectants for hair and skin damage (e.g., WO 9404129), Van den Broeke et al. (1993, Int. J. Radiat. Biol. 63:493–500) did not find topically-applied L-ergothioneine effective in an animal model of UV-induced phototoxic drug binding to epidermal biomolecules. Other proposed in vivo uses have included lowering of circulating lipoprotein (a) levels (U.S. Pat. No. 5,272,166), and inhibiting skin pigmentation, for example, to remove dark spots and freckles (JP 63008335 and JP 61155302).

As described above, numerous disease processes are attributed to the body's adverse reaction to the presence of elevated levels of reactive oxygen species (ROS) described above. In the eye, cataract, macular degeneration and degenerative retinal damage are attributed to ROS. Among other organs and their ROS-related diseases include: lung cancer induced by tobacco combustion products and asbestos; accelerated aging and its manifestations, including skin damage; atherosclerosis; ischemia and reperfusion injury, diseases of the nervous system such as Parkinson disease, Alzheimer disease, muscular dystrophy, multiple sclerosis; other lung diseases including emphysema and bronchopulmonary dysphasia; iron overload diseases such as hemochromatosis and thalassemia; pancreatitis; diabetes; renal diseases including autoimmune nephrotic syndrome and heavy metal-induced nephrotoxicity; and radiation injuries. Certain anti-neoplastic drugs such as adriamycin and bleomycin induce severe oxidative damage, especially to the heart, limiting the patient's exposure to the drug. Redox-active metals such as iron induce oxidative damage to tissues; industrial chemicals and ethanol, by exposure and consumption, induce an array of oxidative damage-related injuries, such as cardiomyopathy and liver damage. Airborne industrial and petrochemical-based pollutants, such as ozone, nitric oxide, radioactive particulates, and halogenated hydrocarbons, induce oxidative damage to the lungs, gastrointestinal tract, and other organs. Radiation poisoning from industrial sources, including leaks from nuclear reactors and exposure to nuclear weapons, are other sources of radiation and radical damage. Other routes of exposure may occur from living or working in proximity to sources of electromagnetic radiation, such as electric power plants and high-voltage power lines, x-ray machines, particle accelerators, radar antennas, radio antennas, and the like, as well as using electronic products and gadgets which emit electromagnetic radiation such as cellular telephones, and television and computer monitors. Protecting mitochondria from these many etiologic agents is desirable.

SUMMARY OF THE INVENTION

It is an objective of the present invention to provide a means for protecting mitochondria from damage by providing methods and compositions by which mammalian mitochondrial membranes are protected.

It is another objective of the invention to provide methods and compositions by which mammalian mitochondria can be protected from oxidative damage.

It is a further objective of the invention to provide methods and compositions which protect mammalian mitochondria from being damaged by the effects of incident sunlight as well as other damaging radiation.

It is yet a further objective of the invention to provide methods and compositions which protect mammalian mitochondria from being damaged by the effects of airborne oxidative toxins, such as are present in industrial pollutants and in petrochemical and tobacco combustion products.

It is as yet another objective of the invention to provide methods and compositions which protects mammalian mitochondria from being damaged by the effects of elevated levels of oxidative compounds and reactive oxygen species which occur in various disease processes, as well as that induced by various therapeutic agents and regimens.

It is another object of the present invention to provide diagnostic tests for determining in a mammal the extent and susceptibility to mitochondrial damage from radiation, radicals, and reactive oxygen species.

Mitochondria are damaged by oxidative damage due to natural and disease processes as well as by the effects of exogenous factors such as incident sunlight, exposure via inhalation to oxidative environmental toxins, electromagnetic radiation, consumption of dietary oxidants, and oxidative-stress-inducing pharmaceuticals, among others. In the present invention, pretreatment or treatment of cells with L-ergothioneine protects mitochondria from such damage and reduces the damage caused to mitochondria by sunlight and that caused by the presence of oxygen radicals. In one non-limiting example, L-ergothioneine is combined in a pharmaceutically-acceptable carrier to form an agent for topical application to the skin. The invention includes methods for treatment using L-ergothioneine administered orally or parenterally. Effective application and delivery of L-ergothioneine is enhanced by encapsulation in a liposome, a preferred embodiment. In one example, a liposome composed of phosphatidyl choline, phosphatidyl ethanolamine, oleic acid and cholesteryl hemisuccinate is used. The liposome-encapsulated L-ergothioneine is also combined with a pharmaceutically-acceptable carrier for topical application.

DETAILED DESCRIPTION OF THE INVENTION

Inhibition of oxidative damage to mitochondria in various tissues of the mammalian body is of therapeutic benefit for the prophylaxis and treatment of many pathological conditions ranging from those responsible for significant morbidity and mortality, such as atherosclerosis and cancer, to those of a less pathological but significant adverse psychological component, such as unsightly changes to the skin as a result of long-term photoaging. In diverse diseases such as cancer, diabetes, atherosclerosis, cataract, and certain neurological diseases, among others, reactive oxygen species (ROS) are implicated in the pathophysiology of the disease. Ischemia, in which tissues are deprived of blood flow and oxygen such as occurs during stroke and myocardial infarction, followed by reperfusion of the ischemic tissue, initiates significant ROS damage to the tissue which is not directly killed during the infarction. Cancer chemotherapeutic agents such as adriamycin and bleomycin induce oxidant damage, as does anti-cancer radiation (e.g., X-ray) therapy . As critical subcellular organelles involved in aerobic energy metabolism and the oxidative reactions therein, mitochondria are sensitive to endogenous and exogenous influences and may be easily damaged or destroyed. Dysfunctional energy metabolism and, more severely, damaged mitochondria, may lead to cell senescence and death, and downstream tissue and organ dysfunction and damage. In the skin, increased oxidative damage as a consequence of UV light exposure can damage the cellular structure of the skin leading to premature, psychologically-debilitating changes related to aging, such as thinning of the skin, wrinkling, and abnormal pigmentation. Exposure of environmental oxidants to the lungs can induce mitochondrial and attendant cellular damage leading to chronic airways obstructive disorders. Exposure to electromagnetic and nuclear radiation also induce oxidative damage.

In accordance with the present invention, protection is afforded to mitochondria by the application or administration of a composition comprising L-ergothioneine (L-ET). Administration to the target cells, tissue, or organ may be parenterally; transmucosally, e.g., orally, nasally, rectally; or transdermally. Parenteral administration is via intravenous injection, and also including, but is not limited to, intraarterial, intramuscular, intradermal, subcutaneous, intraperitoneal, intraventricular, intrathecal and intracranial administration. For example, the composition of the present invention may be infused directly into a tissue or organ that had undergone an infarct, such as the brain or heart following a stroke or heart attack, in order to protect mitochondria in the cells of the ischemic penumbra, those outside of the immediate infarct zone which are not killed during the cessation of blood flow but undergo extensive ROS-mediated damage when blood flow is restored. L-ET may be prepared as a tablet or capsule formulation for oral administration. For topical delivery, a solution of L-ET in water, buffered aqueous solution or other pharmaceutically-acceptable carrier, or in a hydrogel lotion or cream, comprising an emulsion of an aqueous and hydrophobic phase, at a concentration of between 50 $\mu$M and 5 mM, is used. A preferred concentration is about 1 mM. To this may be added ascorbic acid or its salts, or other ingredients, or a combination of these, to make a cosmetically-acceptable formulation. Metals should be kept to a minimum. It may be preferably formulated by encapsulation into a liposome for oral, parenteral, or, preferably, topical administration. As will be seen below, a composition of L-ET within a liposome improves the efficacy of protection of mitochondria from oxidative damage resulting from radiation damage.

It was found unexpectedly that the use of a liposome formulation for L-ET enhances the effectiveness of the compound for the protection of mitochondria. While liposome delivery has been utilized as a pharmaceutical delivery system for many other compounds for a variety of applications [see Langer, *Science* 249:1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, ibid., pp. 317–327; see generally ibid.], subcellular delivery of L-ET in an efficacious form was discovered by the inventor herein and is a preferred embodiment of the compositions and methods of the present invention. The function of the liposome is to increase the delivery of the L-ET to the mitochondria, and distinctly or additionally, to protect the L-ET until it reaches the target cell or tissue. A non-limiting example of a liposome formulation is that formed from phosphatidylcholine, phosphatidylethanolamine, oleic acid and cholesteryl hemisuccinate in a ratio of 2:2:1:5, encapsulating 10 mM L-ET. A final concentration of 1 $\mu$M to 10 mM L-ET is used, preferably about 12 $\mu$M. This final concentration can be achieved by dilution of the purified liposomes in a pharmaceutically-acceptable carrier. Many other suitable liposome formulations are known to the skilled artisan, and may be employed for the purposes of the present invention. For example, see: U.S. Pat. No. 5,190,762; "Method of Administering Proteins to Living Skin Cells" to Yarosh which is incorporated herein by reference. A general discussion of liposomes and liposome technology can be found in a three volume work entitled "Liposome Technology" edited by G. Gregoriadis, 1993, published by CRC Press, Boca Raton, Florida. The pertinent portions of this reference are incorporated herein by reference.

Transdermal delivery of L-ET, either as a liposome formulation or free L-ET, is also contemplated. Various and numerous methods are known in the art for transdermal administration of a drug, e.g., via a transdermal patch. It can be readily appreciated that a transdermal route of administration may be enhanced by use of a dermal penetration enhancer.

In yet another aspect of the present invention, provided are pharmaceutical compositions of L-ET. Such pharmaceutical compositions may be for administration for injection, or for oral, pulmonary, nasal or other forms of administration. In general, comprehended by the invention are pharmaceutical compositions comprising effective amounts of L-ET together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosal, benzyl alcohol) and bulking substances (e.g., lactose, mannitol); incorporation of the material into particulate preparations of polymeric compounds such as polylactic acid, polyglycolic acid, etc. or into liposomes (infra). Hylauronic acid may also be used. Such compositions may influence the physical state, stability, rate of in vivo release, and rate of in vivo clearance of L-ET. The compositions may be prepared in liquid form, or may be in dried powder, such as lyophilized form.

Controlled release oral formulation may be desirable. The drug may be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects.

Also contemplated herein is pulmonary delivery of the pharmaceutical compositions of the present invention, for the treatment or protection of mitochondria from oxidative damage. Pulmonary delivery may be used to treat the lung tissue itself, or serve as a delivery route to the blood stream and thus other locations within the body. A pharmaceutical composition of the present invention is delivered to the lungs of a mammal while inhaling and traverses across the lung epithelial lining to the blood stream. Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

Ophthalmic delivery of the compositions of the present invention are also contemplated for the protection and treatment of mitochondria, for example, in the lens of the eye, in which oxidative damage is believed to account for a high incidence of cataracts. Other ophthalmic uses include treatment or prophylaxis of macular degeneration and degenerative retinal damage.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran. For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

In a further aspect, the L-ET liposomes can cross the blood-brain barrier, which would allow for intravenous or oral administration. Many strategies are available for crossing the blood-brain barrier, including but not limited to, increasing the hydrophobic nature of a molecule; introducing the molecule as a conjugate to a carrier, such as transferrin, targeted to a receptor in the blood-brain barrier; and the like. In another embodiment, the molecule can be administered intracranially or, more preferably, intraventricularly. In yet another embodiment, L-ET can be administered in a liposome targeted to the blood-brain barrier.

A subject in whom administration of L-ET is an effective therapeutic regiment for mitochondrial protection is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The protection of mitochondria from oxidative damage may be used for the prevention and treatment of a number of disorders, including effects of solar, electromagnetic and nuclear radiation to the body, disease processes, exposure to pollutants including tobacco combustion products, and protection against the damaging effects of certain pharmaceuticals whose mechanisms of action involve generation of reactive oxygen species and other radicals. For example, certain anti-neoplastic agents induce oxidative radicals as their mechanism of action, but a significant and limiting side effect in patients is cardiotoxicity; higher doses and thus increased anti-cancer efficacy is achievable by protecting the mitochondria of the heart and other tissues with the compositions and methods of the present invention. In addition, various types of radiation used for anti-cancer therapy, as an alternative or adjunct to surgery, induces significant damage to tissues; prior administration of L-ET may be used to reduce or prevent the toxicity of radiation therapy to the body. It may further be used in combination with fibrinolytic therapy, such as tissue plasminogen activator or streptokinase, wherein clots in obstructed blood vessels causing stroke and heart attack are dissolved. Protection of tissues from ROS arising as a result of reperfusion is an object of the present invention.

Furthermore, numerous disease processes involve reactive oxygen species. In the eye, cataract, macular degeneration and degenerative retinal damage are attributed to ROS and may be treated with topical, oral or parenterally-administered L-ET. A liposome formulation is preferred. ROS-related diseases of the lungs such as emphysema and bronchopulmonary dysphasia and including pathology induced by inhalation of tobacco combustion products and asbestos may be treated by an aerosolized form of L-ET as described above. Various diseases of the nervous system such as Parkinson disease, Alzheimer disease, muscular dystrophy, and multiple sclerosis may be treatable by oral or parenteral formulations or direct delivery to the central nervous system via intrathecal, intraventricular and intracranial administration. Iron overload diseases such as hemochromatosis and thalassemia may also be treated by the compositions and methods of the present invention. Other diseases include pancreatitis; diabetes; renal diseases including autoimmune nephrotic syndrome and heavy metal-induced nephrotoxicity; and radiation injuries. Local and system injury as a result of burns involve ROS damage.

In addition to the aforementioned therapeutic and prophylactic uses of the compositions of the present invention, various diagnostic utilities are also contemplated. The potential of L-ergothioneine to protect a mammal from mitochondrial damage and the level of L-ET necessary to afford protection may be assessed in vitro exposing aliquots of a cellular sample from said mammal to the damaging agent or condition, said aliquots containing various concentrations of L-ET. The damage to mitochondria of the various aliquots is determined, as well as the lowest concentration, if any, of L-ET providing sufficient protection from damage. To determine the degree of therapeutic benefit of L-ET to a mammal after exposure to a mitochondrial damaging agent, a similar diagnostic test as described above may be employed, with a variation in that the various concentrations of L-ET are applied to the cellular sample aliquots after exposure to the mitochondrial damaging agent. In another embodiment, the extent of exposure of a mammal to ROS may be assessed by determining the effect of L-ET on a sample of cells taken from the mammal. These diagnostic utilities further offer assistance in selecting a effective therapeutic dose of L-ET.

In a further embodiment, the ability of L-ET to protect a cellular sample from the damaging effects of a therapeutic regimen that causes oxidative damage, such as an anti-neoplastic agent or radiation therapy to be administered to a mammal with cancer, can be performed in vitro by combining the anti-neoplastic agent with various concentrations of L-ET, applying the combination to identical aliquots of a cellular sample from a mammal, and determining the extent of mitochondrial damage in said series of samples. These data may be used to determine an effective dose of L-ET to prevent mitochondrial damage in the non-diseased cells of said mammal. In a parallel manner using a sample of diseased or cancerous cells from said mammal, it may be determined whether L-ET will effect any diminution of the anti-cancer activity of said anti-cancer agent; based on these two tests, a level of L-ET for co-administration with the anti-cancer agent may be selected to provide optimal protection of the non-diseased cells of the mammal from the anti-cancer agent while providing maximum anti-cancer therapy. These are non-limiting examples of useful diagnostic tests assessing the prophylactic and therapeutic benefits of the compositions and methods of the present invention.

Application of L-ET and its effect on mitochondrial damage is demonstrated by the following experimental examples in which mouse keratinocytes are treated with unencapsulated or liposome-encapsulated L-ET. The mitochondria are then subjected to the potentially damaging effects of UV-B light and to alloxan (which is known to induce oxygen radicals) and the results measured. Damage to mitochondria were detected by two methods: 1) the MTT assay and 2) the JC-1 assay.

EXAMPLE I

UV-B Light: Mouse keratinocytes were pretreated with different concentrations of L-ergothioneine (unencapsulated) and then exposed to ultraviolet B radiation (UV-B), the shorter wavelength range of UV light present in sunlight which is responsible for significant photodamage to the skin. The light was generated by a FS20 sunlamp filtered with 2 sheets of Kodicell to eliminate light having a wavelength less than 280 nm.

MTT Assay: This assay measures the specific activity of mitochondria to cleave the tetrazolium ring of the soluble dye MTT [3-(4,5-dimethylthiazol-2-yl)-2,5-diphenyl tetrazolium bromide] to form the insoluble blue formazan form. Living mitochondria metabolize MTT and make the blue formazan; dead mitochondria immediately stop forming blue formazan. In the MTT assay, mammalian cells are pretreated with L-ergothioneine and then treated with the mitochondrial damaging agent, in this example UV-B. MTT is then added and the formation of the blue dye is measured spectrophotometrically.

Results: Table I provides the percent optical density of the formazan blue present relative to unexposed (control) mitochondria in cells for various UV-B levels, expressed as joules per square meter, and L-ergothioneine concentrations.

TABLE I

| UV-B | L-ergothioneine concentration | | | |
|---|---|---|---|---|
| $(J/m^2)$ | 0 mM | 0.1 mM | 0.5 mM | 1 mM |
| 0 | 100.0 | 100.0 | 100.0 | 100.0 |
| 100 | 84.2 | 95.7 | 97.2 | 97.1 |
| 200 | 80.7 | 97.0 | 99.4 | 103.9 |
| 500 | 79.9 | 91.0 | 90.8 | 96.0 |

These data show that in the absence of L-ET, increasing UV-B irradiation intensity results in a decreasing numbers of living mitochondria in the keratinocytes, as shown by the dose-responsive decreasing level of conversion of MTT to formazan. Ultraviolet-irradiated keratinocytes are protected by L-ergothioneine: at 100 and 200 $J/m^2$, all three levels of L-ET have maintained greater than 95% mitochondrial viability; at the highest UV-B dose, L-ET still protected the mitochondria.

EXAMPLE 2

Alloxan: Mouse keratinocytes were pretreated with various concentrations of L-ergothioneine (unencapsulated) and then exposed to alloxan at various concentrations.

MTT Assay: The effect of alloxan on the pretreated mitochondria was determined by the MTT assay as in Example 1.

Results: Table 2 provides the percent optical density of the formazan blue present relative to unexposed (control) mitochondria in cells for various alloxan concentrations and L-ergothioneine concentrations.

TABLE 2

| Alloxan (mM) | L-ergothioneine concentration | | | |
|---|---|---|---|---|
| | 0 mM | 0.1 mM | 0.5 mM | 1 mM |
| 0 | 100.0 | 100.0 | 100.0 | 100.0 |
| 0.625 | 81.6 | 86.3 | 88.3 | 91.2 |
| 1.25 | 76.5 | 80.8 | 81.0 | 86.5 |
| 2.5 | 77.1 | 81.1 | 81.0 | 82.9 |
| 5 | 69. | 73.3 | 73.3 | 67.8 |
| 10 | 70.7 | 74.9 | 74.1 | 68.5 |
| 20 | 74.5 | 79.1 | 78.4 | 72.7 |
| 40 | 69.2 | 73.3 | 72.3 | 66.6 |

Alloxan induces oxidative damage to mitochondria; a dose-responsive reduction in mitochondrial viability can be seen up to a level of 5 mM, above which the damage has plateaued. In the dose-responsive portion of the curve, L-ergothioneine afforded protection from oxidative damage.

EXAMPLE 3

Mouse keratinocytes were pretreated with L-ergothioneine, both unencapsulated and encapsulated in liposomes (prepared as described below), at a final concentration of 12.5 µM. A control group was not treated with L-ergothioneine. The mouse keratinocytes were then exposed to UV-B as in Example 1.

Liposome Encapsulation: The L-ergothioneine was encapsulated into liposomes composed of phosphatidyl choline, phosphatidyl ethanolamine, oleic acid and cholesteryl hemisuccinate in a ratio of 2:2:1:5. To calculate the concentration of entrapped L-ergothioneine, the liposomes are extracted with chloroform, and the $OD_{258}$ is measured in the aqueous layer. The concentration of L-ergothioneine is calculated using the $\epsilon_{258}$ of L-ergothioneine of 14,500. The final concentration of L-ET in the purified liposome was about 1.1 mM. This concentration was reduced by diluting the liposomes with cell culture media to a final concentration of 12.5 µM in the media. Unencapsulated L-ergothioneine was adjusted to the same concentration by dilution.

The effect of the UV-B on the pretreated and untreated mitochondria was determined by the MTT assay as in Example 1.

Results: Table 3 provides the percent optical density of the formazan blue present in each case relative to unexposed (control) mitochondria in cells for various UV-B levels.

TABLE 3

| UV-B | L-ergothioneine at 12.5 µM | | |
|---|---|---|---|
| $(J/m^2)$ | Encapsulated L-ET | Unencapsulated L-ET | Without L-ET |
| 0 | 100.0 | 100.0 | 100.0 |
| 100 | 106.8 | 89.9 | 75.4 |
| 500 | 110.3 | 89.9 | 76.8 |

In the absence of L-ergothioneine, keratinocytes showed significant mitochondrial damage at both UV-B doses. Unencapsulated L-ET afforded significant but not complete protection under these conditions, but complete protection was afforded by the encapsulated formulation of L-ET, at the same concentration. Thus, the liposome formulation of L-ET provides superior protection.

EXAMPLE 4

Alloxan: Mouse keratinocytes were pretreated with L-ergothioneine (unencapsulated) at 1 mM and then treated with 8 mM alloxan. One day after treatment with L-ergothioneine, the cells were treated for 10 minutes with JC-1 and the cells examined by fluorescence microscopy.

JC-1 Assay: The JC-1 assay makes use of the fluorescent dye JC-1 (5,5',6,6'-tetrachloro-1,1',3,3'-tetraethylbenzimidazoylcarbocyanine iodide) (Molecular Probes, Inc., Eugene, OR). This dye immediately and specifically intercalates into mitochondrial membranes. In living, charged membranes the JC-1 dye is maintained in the membrane as a monomer, and fluoresces green. When the mitochondrial membrane is damaged, aggregation of the JC-1 dye into J-aggregates occurs and the fluorescence changes to orange. Orange coloration is then characteristic of mitochondrial membrane damage.

Results: Untreated control cells were predominantly green. Cells treated with alloxan alone showed significant patches of orange. Cells treated with alloxan and L-ergothioneine showed much less orange than cells treated with alloxan alone. Cells treated with L-ergothioneine alone showed green fluorescence.

Thus, using a different means of determining mitochondrial viability, the protection afforded mitochondria by L-ET is confirmed.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

Various citation to the literature present above are incorporated herein by reference.

What is claimed is:

1. A method for the protection of mitochondria from damage caused by radiation, radicals and reactive oxygen species, said method comprising making available to said mitochondria a composition comprising L-ergothioneine in an amount effective to protect said mitochondria, and a pharmaceutically-acceptable carrier.

2. The method of claim 1 wherein said composition comprises L-ergothioneine at a concentration in the range of 50 µM to 5 mM.

3. The method of claim 1 wherein the L-ergothioneine is at a concentration of about 1 mM.

4. The method of claim 1, wherein said composition is dispersed within a liposome.

5. The method of claim 3 wherein said liposome is prepared from a composition comprising phosphatidyl choline, phosphatidyl ethanolamine, oleic acid, and cholesteryl hemisuccinate in a ratio of about 2:2:1:5.

6. The method of claim 5 wherein the L-ergothioneine is present at a concentration in the range of 1 µM to 10 mM.

7. The method or claim 6 wherein the L-ergothioneine is present at a concentration of about 12 µM.

8. The method of claim 1 wherein said composition is made available to said mitochondria by parenteral, topical, transmucosal, pulmonary, or transdermal administration of said composition thereto.

9. The method of claim 8 wherein said transdermal administration comprises topical application to a skin surface.

10. The method of claim 9 wherein said carrier is a hydrogel lotion.

11. The method of claim 8 wherein said transmucosal administration is selected from the group consisting of oral, rectal, and nasal administration.

12. The method of claim 8 wherein said parenteral administration is selected from the group consisting of intravenous, subcutaneous, intraarterial, intramuscular, intraperitoneal, intrathecal, intracranial, and intraventricular administration.

13. The method of claim 1 wherein said damage results from exposure to airborne toxins selected from the group consisting of tobacco combustion products, industrial pollutants, petroleum combustion products, ozone, nitric oxide, radioactive particulates, and combinations thereof.

14. The method of claim 1 wherein said damage results from exposure to the group consisting of ultraviolet radiation, solar radiation, suntanning radiation, thermal radiation, sunburning radiation, gamma radiation, microwave radiation, electromagnetic radiation, nuclear radiation, and combinations thereof.

15. The method of claim 1 wherein said damage is pathologically causative in a disease or condition selected from the group consisting of cataract, macular degeneration, degenerative retinal damage, lung cancer, skin cancer, melanoma, sunburn, radiation poisoning, asbestosis, atherosclerosis, Parkinson disease, Alzheimer disease, muscular dystrophy, multiple sclerosis, burns, emphysema, bronchopulmonary dysphasia, iron overload diseases, hemochromatosis, thalassemia, pancreatitis, diabetes, autoimmune nephrotic syndrome, heavy metal-induced nephrotoxicity, and radiation injury.

16. The method of claim 1 wherein said damage is induced by the exposure to or consumption of nuclear waste, fallout, industrial chemicals or ethanol.

17. The method of claim 1 wherein said damage is caused by a factor selected from the group consisting of reactive oxygen species, radicals, free radicals, oxidative stress, oxidative damage, and combinations thereof.

18. A method for the protection of mitochondria from damage caused by the therapeutic administration of pharmaceutical agents or radiation, wherein said method comprises making available to said mitochondria a composition comprising L-ergothioneine in an amount effective to protect said mitochondria, and a pharmaceutically-acceptable carrier, said composition co-administered with said therapeutic agent or radiation treatment.

19. The method of claim 18 wherein said therapeutic agent is selected from the group consisting of anti-cancer agents, anti-cancer radiation therapy, fibrinolytic therapy, and combinations thereof.

20. The method of claim 18 wherein said composition is disposed within a liposome.

21. A composition providing protection to mitochondria from damaging radiation, radicals, and reactive oxygen species comprising L-ergothioneine disposed within a liposome in a pharmaceutially-acceptable carrier.

22. The composition of claim 21 wherein said carrier is a hydrogel lotion.

23. The composition of claim 21 wherein the L-ergothioneine is present at a final concentration in the range of 50 $\mu$M to 5 mM.

24. The composition of claim 23 wherein the L-ergothioneine is present at a final concentration of about 1 mM.

25. A composition providing protection to mitochondria from damaging radiation, radicals and reactive oxygen species comprising L-ergothioneine at least partially encapsulated in a liposome.

26. The composition of claim 25 wherein said liposome is prepared from a liposome-forming composition comprising phosphatidyl choline, phosphatidyl ethanolamine, oleic acid, and cholesteryl hemisuccinate in a ratio of about 2:2:1:5.

27. The composition of claim 25 wherein said L-ergothioneine is present at a concentration in the range of 1 $\mu$M to 5 mM.

28. The composition of claim 27 wherein said L-ergothioneine is present at a concentration of about 12 $\mu$M.

29. A method for determining the level of radiation, radical or reactive oxygen species damage to a mammal comprising the sequential steps of:
 (a) isolating a cellular sample from said mammal;
 (b) dividing said cellular sample into a series of identical aliquots;
 (c) exposing each of said aliquots to one of a range of concentrations of L-ergothioneine in a pharmaceutically-acceptable carrier;
 (c) determining the extent of damage to mitochondria in said aliquots; and
 (d) using a predetermined correlation between L-ergothioneine level and the degree of inhibition of various extents of mitochondrial damage in a cellular sample from a test mammal exposed to radiation, radicals or reactive oxygen species, deriving the extent of damage to said mammal.

30. A method for determining the susceptibility of a mammal to radiation, radical or reactive oxygen species damage comprising the sequential steps of:
 (a) isolating a cellular sample from said mammal;
 (b) exposing said cellular sample to radiation, radicals or reactive oxygen species;
 (b) dividing said cellular sample into a series of identical aliquots;
 (c) exposing each of said aliquots to one of a series of compositions comprising various concentrations of L-ergothioneine in a pharmaceutically-acceptable carrier;
 (d) determining the extent of damage to mitochondria in said aliquots and identifying the concentration or concentrations of L-ergothioneine that inhibits said mitochondrial damage;
 (e) comparing said concentrations to a predetermined relationship between the L-ergothioneine concentration and the extent of protection from mitochondrial damage of mammalian cells pre-exposed to radiation, radicals or reactive oxygen species, and thereby deriving the susceptibility of said mammal to said damage.

31. A method for determining in a mammal the extent of protection afforded by L-ergothioneine to radiation, radical or reactive oxygen species damage comprising the sequential steps of:
 (a) isolating a cellular sample from said mammal;
 (b) dividing said cellular sample into a series of aliquots;
 (c) exposing each of said aliquots to one of a series of compositions comprising various concentrations of L-ergothioneine in a pharmaceutically-acceptable carrier;
 (d) exposing said aliquots to radiation, radicals, or reactive oxygen species;
 (e) determining the extent of damage to mitochondria in said aliquots and identifying the concentration or concentrations of L-ergothioneine that inhibits said mitochondrial damage;
 (f) comparing the level of said damage to the L-ergothioneine concentrations to a predetermined relationship between the L-ergothioneine concentration and the extent of protection from mitochondrial damage of mammalian cells pre-exposed to radiation, radicals or reactive oxygen species, and thereby deriving the degree of protection of said mammal to said damage.

32. The method of claim 31 used for determining an efficacious dose of L-ergothioneine for treatment of a mammal to be exposed to radiation, radicals or reactive oxygen species.

* * * * *